US011426515B2

(12) United States Patent
Azapagic et al.

(10) Patent No.: US 11,426,515 B2
(45) Date of Patent: Aug. 30, 2022

(54) INFUSION PUMP CASSETTE HAVING INTEGRATED PINCH CLIP OCCLUDER (71) Applicant: Zevex, Inc., Salt Lake City, UT (US)

(72) Inventors: Azur Azapagic, Cottonwood Heights, UT (US); Kent F. Beck, Layton, UT (US)

(73) Assignee: Zevex, Inc., Salt Lake City, UT (US)

( * ) Notice: Subject to any disclaimer, the term of this patent is extended or adjusted under 35 U.S.C. 154(b) by 357 days.

(21) Appl. No.: 16/522,325

(22) Filed: Jul. 25, 2019

(65) Prior Publication Data

US 2021/0023297 A1  Jan. 28, 2021

(51) Int. Cl.
*A61M 5/168* (2006.01)
*A61M 5/142* (2006.01)
A61M 5/14 (2006.01)

(52) U.S. Cl.
CPC .... *A61M 5/16813* (2013.01); *A61M 5/14212* (2013.01); *A61M 2005/1402* (2013.01); *A61M 2205/128* (2013.01)

(58) Field of Classification Search
CPC ............ A61M 2205/128; A61M 39/28; A61M 39/26; A61M 5/14228; A61M 2205/12; A61M 2205/121; A61M 5/142; A61M 2205/3331; A61M 5/14212
See application file for complete search history.

(56) References Cited

U.S. PATENT DOCUMENTS

| 3,918,854 | A |   | 11/1975 | Catarious et al. |
| 4,537,561 | A | * | 8/1985  | Xanthopoulos ....... A61M 5/142 128/DIG. 12 |
| 4,689,043 | A |   | 8/1987  | Bisha |
| 4,944,485 | A | * | 7/1990  | Daoud ................ A61M 39/284 137/560 |
| 5,330,431 | A |   | 7/1994  | Herskowitz |
| 5,401,256 | A |   | 3/1995  | Stone et al. |
| 5,620,312 | A | * | 4/1997  | Hyman ................ A61M 5/142 417/474 |
| D389,228  | S |   | 1/1998  | Winterer et al. |

(Continued)

FOREIGN PATENT DOCUMENTS

| EP | 1557187 A1 | 7/2005 |
| JP | 3133453 U  | 7/2007 |

(Continued)

*Primary Examiner* — Nilay J Shah
(74) *Attorney, Agent, or Firm* — Hodgson Russ LLP (57) ABSTRACT

A cassette usable with an infusion pump includes a monolithic cassette body and a segment of resiliently deformable tubing for conveying a flow of liquid. The monolithic cassette body has an integrally formed free-flow protection device including a fixed pinch element and a deflectable pinch arm having a movable pinch element. The pinch arm normally resides in a closed position wherein the pinch elements cooperate to deform the tubing segment to stop flow. The pinch arm is resiliently deflectable away from the closed position to an open position permitting flow. Deflection of the pinch arm away from the closed position spring biases the pinch arm for automatic return to the closed position. The pinch arm may be moved to the open position by operating a door of the pump when the cassette is loaded in the pump, and manually for priming when the cassette is not loaded in the pump.

17 Claims, 5 Drawing Sheets

(56) References Cited

U.S. PATENT DOCUMENTS

| | | |
|---|---|---|
| 5,704,584 A | 1/1998 | Winterer et al. |
| 5,954,485 A | 9/1999 | Johnson et al. |
| 6,203,528 B1 | 3/2001 | Deckert et al. |
| 8,551,057 B2 | 10/2013 | Gagliardoni et al. |
| 8,920,144 B2 | 12/2014 | Rotem et al. |
| 8,986,252 B2 | 3/2015 | Cummings et al. |
| 9,017,297 B2 * | 4/2015 | Travis .................. A61M 39/28 |
| | | 604/250 |
| 9,333,290 B2 | 5/2016 | Rotem |
| 9,581,152 B2 | 2/2017 | Rotem et al. |
| 9,616,170 B2 * | 4/2017 | Nakanishi ......... A61M 5/14228 |
| 2003/0040700 A1 | 2/2003 | Hickle et al. |
| 2004/0094147 A1 | 5/2004 | Schyra et al. |
| 2005/0214146 A1 | 9/2005 | Corwin et al. |
| 2007/0265559 A1 * | 11/2007 | Kunishige ......... A61M 5/16831 |
| | | 604/7 |
| 2009/0221964 A1 * | 9/2009 | Rotem ............. A61M 5/16813 |
| | | 604/151 |
| 2010/0036322 A1 | 2/2010 | Rotem |
| 2010/0082001 A1 * | 4/2010 | Beck ................... A61J 15/0076 |
| | | 604/250 |
| 2011/0313358 A1 | 12/2011 | Hariharesan et al. |
| 2012/0083737 A1 | 4/2012 | Beck |
| 2012/0136305 A1 | 5/2012 | Gagliardoni et al. |
| 2012/0213646 A1 | 8/2012 | Shipman |
| 2012/0266965 A1 | 10/2012 | Hariharesan et al. |
| 2013/0267899 A1 | 10/2013 | Robert et al. |
| 2014/0276424 A1 | 9/2014 | Davis et al. |
| 2015/0285404 A1 | 10/2015 | Koyama et al. |

FOREIGN PATENT DOCUMENTS

| | | | |
|---|---|---|---|
| WO | WO-2010023913 A1 * | 3/2010 | ......... A61M 39/281 |
| WO | 2010101783 A2 | 9/2010 | |
| WO | 2014184986 A1 | 11/2014 | |

* cited by examiner

INFUSION PUMP CASSETTE HAVING INTEGRATED PINCH CLIP OCCLUDER

FIELD OF THE INVENTION

The present invention relates to infusion pumps and cassettes removably loadable therein.

BACKGROUND OF THE INVENTION

Programmable infusion pumps are used to carry out controlled delivery of liquid food for enteral feeding and liquid medications for various purposes such as pain management. In a common arrangement, an infusion pump receives a disposable administration set comprising flexible tubing through which an infusion liquid is pumped. The administration set may comprise a cassette through which a resiliently deformable tubing segment extends, wherein the tubing segment has an upstream inflow end connected to tubing coming from a supply source of the infusion liquid and a downstream outflow end connected to tubing that leads to a patient. The resiliently deformable tubing segment is designed to be engaged by a pumping mechanism of the infusion pump. The cassette is removably loadable in the pump in a predetermined position in which the tubing segment is placed near the pumping mechanism to enable the pumping mechanism to act upon the tubing segment to drive liquid flow through the tubing.

As a safety feature to protect the patient, it is known to provide a free-flow protection device as part of the administration set to automatically stop flow of infusion liquid through the tubing if the cassette is not properly loaded in the pump. Free-flow protection devices of the prior art have various forms, including spring-biased pinch clamps, slide clamps, and in-line occluders. When the cassette is properly loaded in the pump, the free-flow protection device is disabled and typically sits idle until needed.

Spring-biased pinch clamps provide reliable free-flow protection, and have advantages over in-line occluders and slide clamps. Unlike in-line occluders, which have a stop valve within the lumen of the tubing segment, spring-biased pinch clamps do not interfere with the flow of thicker nutritional liquids. Unlike slide clamps, which require application of an external force to move the slide clamp from an open position to a closed position, spring-biased pinch clamps are biased to automatically assume a closed position in the absence of an external force needed to open the pinch clamp. Despite these advantages, spring-biased pinch clamps have the drawback that they are mechanically complex to manufacture and assemble. A spring-biased pinch clamp may have three parts: a main body, a separate plunger movable with respect to the main body, and a spring element for biasing the plunger relative to the main body. These parts are manufactured separately and must then be assembled, thereby adding cost to the cassette.

SUMMARY OF THE INVENTION

The present disclosure provides a cassette for use with an infusion pump. The cassette may generally comprise a monolithic cassette body and a segment of resiliently deformable tubing mounted to the cassette body for conveying a flow of liquid. The monolithic cassette body may include a fixed pinch element, and a deflectable pinch arm having a movable pinch element. The pinch arm may normally reside in a closed position in which the movable pinch element cooperates with the fixed pinch element to deform the tubing segment to stop the flow of liquid. The pinch arm may be resiliently deflectable away from the closed position to an open position in which the movable pinch element is positioned relative to the fixed pinch element such that the flow of liquid is permitted, wherein deflection of the pinch arm away from the closed position spring biases the pinch arm toward the closed position. Thus, the monolithic cassette body has an integrally formed free-flow protection device.

In an aspect of the disclosure, the cassette body may include a platen surface, and deflection of the pinch arm from the closed position to the open position may displace the movable pinch element in a lateral direction relative to the platen surface and the tubing segment. In one embodiment, the platen surface may be convex, for example trapezoidal.

In another aspect of the disclosure, the cassette body may include a wall having an opening therethrough, the pinch arm may have a first portion cantilevered outwardly from the wall to extend away from the tubing segment and a second portion arranged to extend inwardly through the opening, and the movable pinch element may be located on the second portion of the pinch arm. The pinch arm may be deflectable away from the closed position by forcing the first portion of the pinch arm toward the wall.

In another aspect of the disclosure, the cassette may further comprise a spring received by the cassette body, wherein the spring additionally spring biases the pinch arm toward the closed position when the pinch arm is deflected away from the closed position. In one embodiment, the spring may be a leaf spring. The leaf spring may include a proximal end and a distal end, and the cassette body may include a first slot adjacent the wall and a second slot adjacent the pinch arm, wherein the first and second slots respectively receive the proximal and distal ends of the leaf spring.

The disclosure also provides fluid delivery system comprising a pump in combination with a cassette as summarized above. The pump may comprise a cassette interface and a pump door movable relative to the cassette interface between a loading position and a pumping position. When the cassette is received by the cassette interface of the pump, movement of the pump door from the loading position to the pumping position may cause the pump door to deflect the pinch arm from the closed position to the open position, and subsequent movement of the pump door from the pumping position to the loading position may cause the pinch arm to automatically return from the open position to the closed position.

BRIEF DESCRIPTION OF THE DRAWINGS

The nature and mode of operation of the present invention will now be more fully described in the following detailed description taken with the accompanying drawing figures, in which.

DETAILED DESCRIPTION OF THE INVENTION

Figure 1:
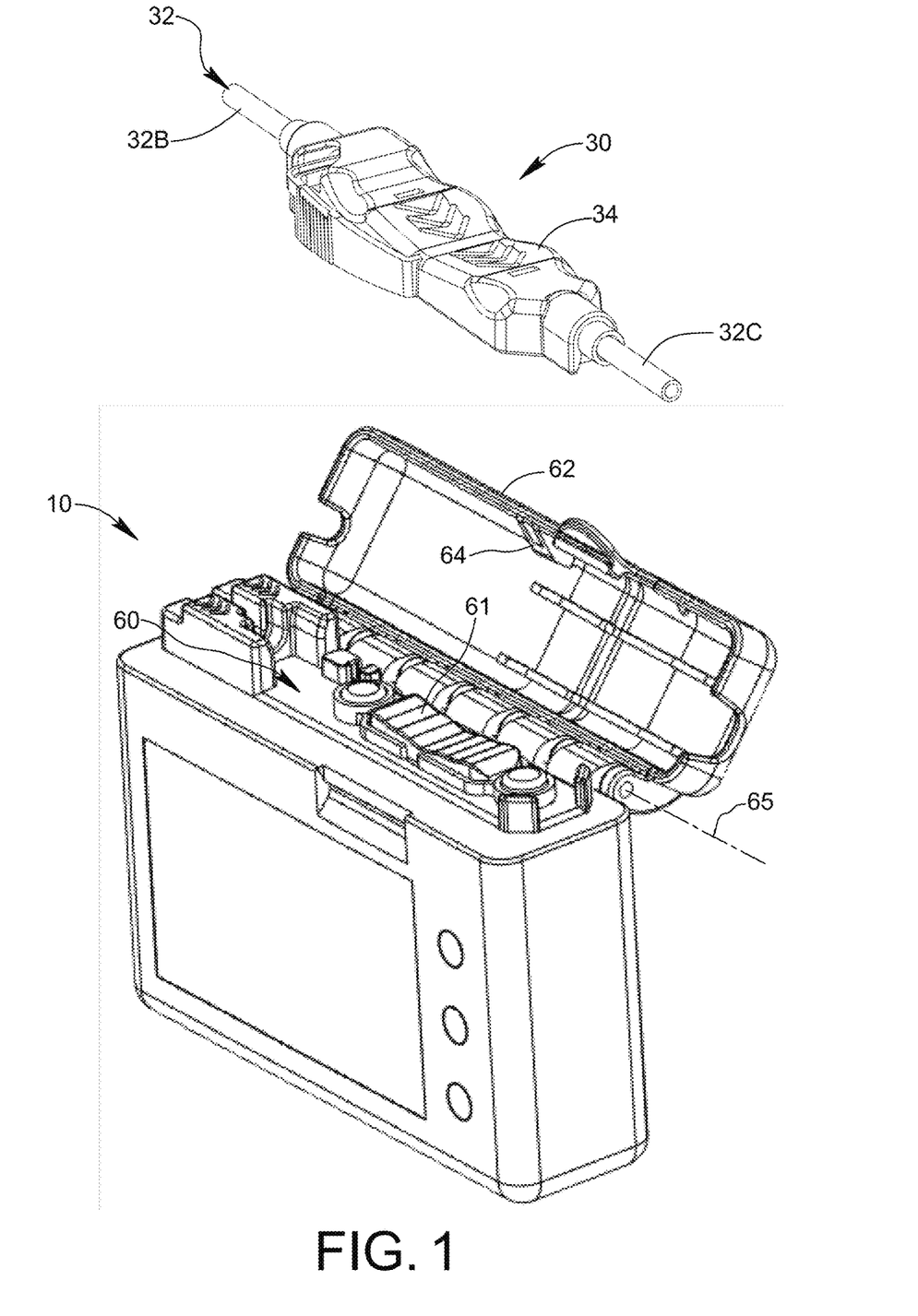
FIG. 1 is an exploded perspective view showing an infusion pump and a portion of an administration set formed in accordance with an embodiment of the present disclosure.
Figure 2:
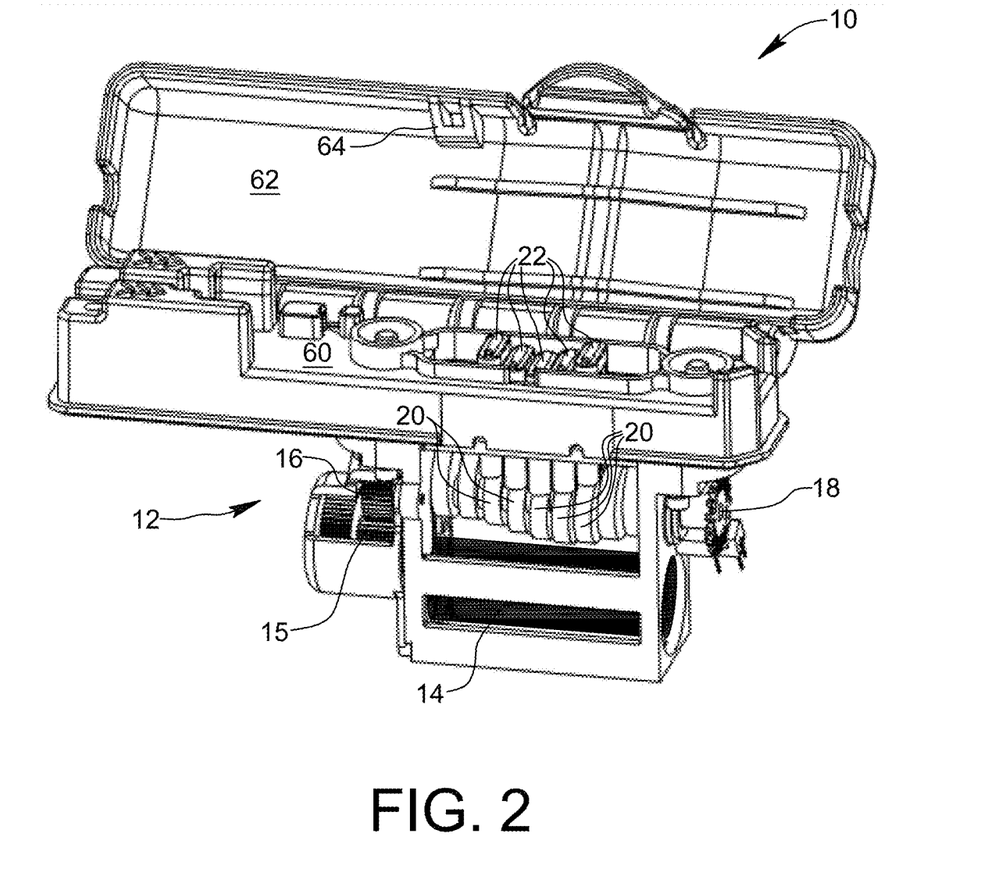
FIG. 2 is a view of the infusion pump shown in FIG. 1 with a housing of the pump removed to reveal internal components of the pump.

FIG. 1 shows an infusion pump 10 and part of a disposable administration set 30 designed to be removably received by infusion pump 10. As best seen in FIG. 2, infusion pump 10 includes a pumping mechanism 12 having an electric motor 14 coupled to a drive gear 15 meshed with a driven gear 16 which is fixed to a camshaft 18. A plurality of eccentric cams 20 are mounted on camshaft 18 for rotation with the camshaft, wherein each cam 20 is arranged to engage a respective pumping finger 22. As may be understood, motor 14 is operable to rotate camshaft 18 and cams 20 about the axis of camshaft 18 such that each of the pumping fingers 22 moves radially in a reciprocating fashion away from and toward camshaft 18. Eccentric cams 20 may be configured such that motion of the pumping fingers 22 provides a cyclical peristaltic pumping action along a longitudinal direction of pumping mechanism 12, i.e. in a direction parallel to the axis of camshaft 18. Persons skilled in the art of infusion pumps will recognize that pumping mechanism 12 may have a different configuration from the one shown and described above. For example, pumping mechanism 12 may be embodied as a rotary pumping mechanism having a motor-driven rotary carrying pumping elements angularly-spaced about a rotational axis of the rotor for providing peristaltic pumping action. By way of further example, pumping mechanism 12 may be configured as a curvilinear pumping mechanism having a single motor-driven rotary cam for causing reciprocating motion of a plurality of pumping fingers in generally radial directions relative to a rotational axis of the rotary cam.

As shown in FIG. 1, administration set 30 comprises tubing 32 for conveying an infusion liquid, and a cassette 34 loadable into infusion pump 10. Tubing 32 may include a resiliently deformable tubing segment 32A, visible in FIGS. 3 and 4, which may be provided as part of cassette 34 and is intended to be operatively engaged by pumping mechanism 12 of infusion pump 10 when cassette 34 is loaded in the pump. Tubing 32 may additionally include upstream tubing 32B coming from a source of infusion liquid (not shown) and connected to an inflow end of tubing segment 32A, and downstream tubing 32C connected to an outflow end of tubing segment 32A and leading to a patient (not shown). Tubing segment 32A may be made of a different material than upstream tubing 32B and downstream tubing 32C, wherein the material of tubing segment 32A is chosen to have desired elasticity and flow parameters when engaged by pumping mechanism 12. For example, tubing segment may be made of soft PVC or silicone, and tubing 32B, 32C may be standard PVC administration set tubing fixed to opposite ends of tubing segment 32A by adhesive.

Figure 3A:
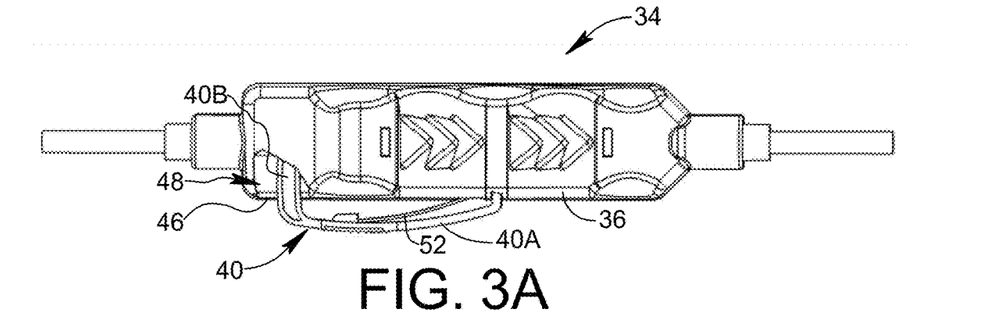
FIG. 3A is a top plan view of a cassette of the administration set shown in FIG. 1, wherein a pinch arm of the cassette is shown in its closed position.
Figure 3B:
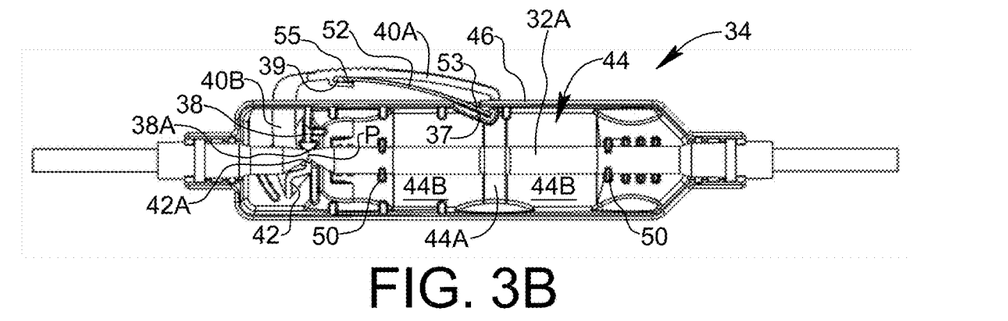
FIG. 3B is a bottom plan view of the cassette shown in FIG. 3A.
Figure 4A:
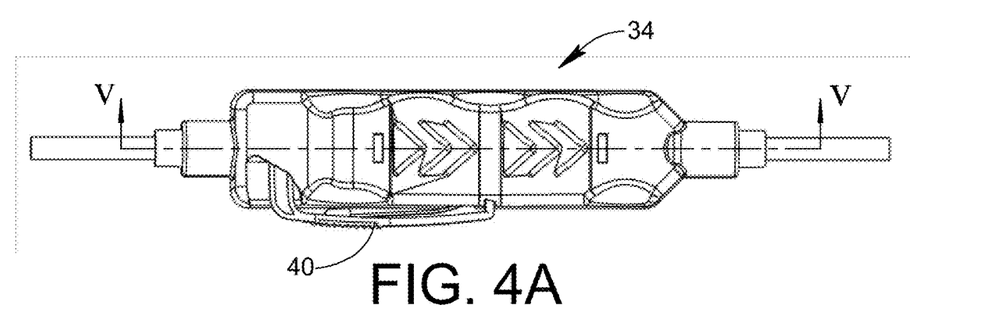
FIG. 4A is another top plan view of the cassette, wherein the pinch arm of the cassette is shown in its open position.
Figure 4B:
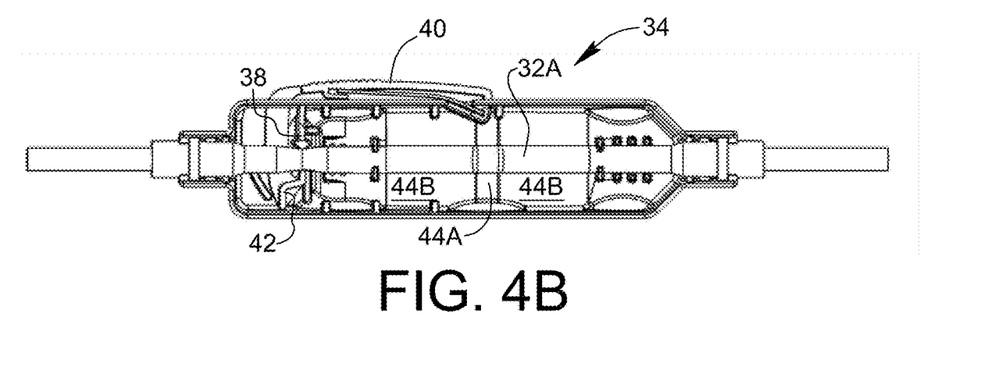
FIG. 4B is a bottom plan view of the cassette shown in FIG. 4A.

Cassette 34 of the present embodiment is now described with reference to FIGS. 3 and 4. In addition to tubing segment 32A, cassette 34 comprises a cassette body 36 which is monolithic. As used herein, the term "monolithic" means molded as a single homogenous piece or additively manufactured as a single homogenous piece.

Monolithic cassette body 36 comprises a free-flow protection device integrally formed as part of the monolithic cassette body. In the depicted embodiment, the free-flow-protection device includes a fixed pinch element 38 and a pinch arm 40 having a movable pinch element 42. Pinch arm 40 normally resides in a closed position illustrated in FIG. 3 in which movable pinch element 42 cooperates with fixed pinch element 38 to deform tubing segment 32A to stop the flow of liquid through the tubing segment. Pinch arm 40 is resiliently deflectable away from the closed position to an open position, illustrated in FIG. 4, in which movable pinch element 42 is positioned relative to fixed pinch element 38 such that the flow of liquid through tubing segment 32A is permitted, wherein deflection of pinch arm 40 away from the closed position spring biases the pinch arm toward the closed position.

Figure 5:
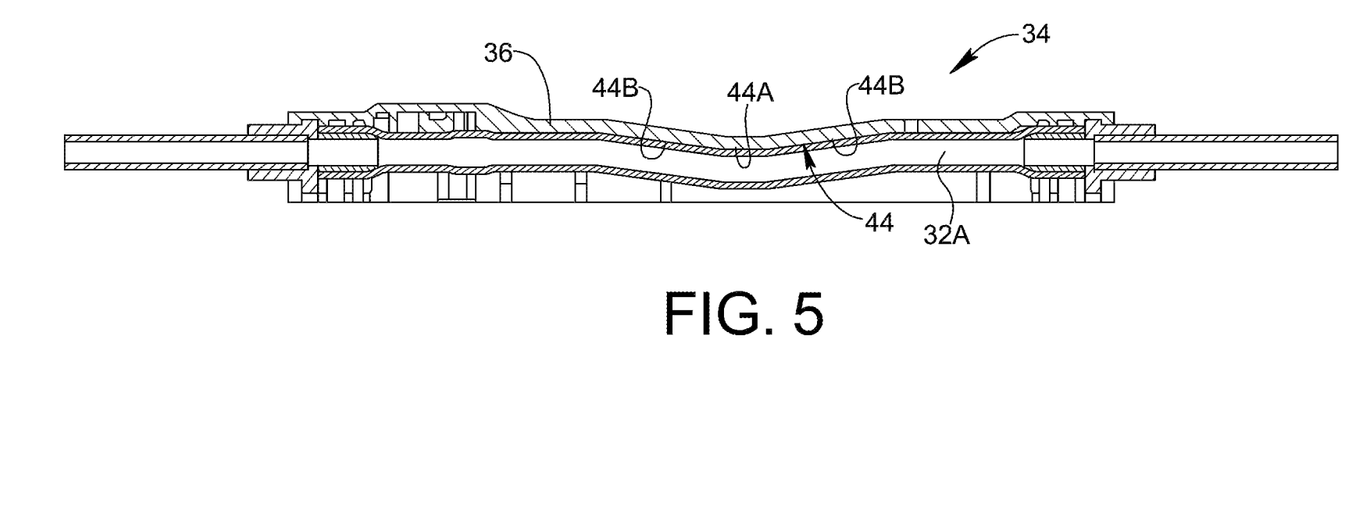
FIG. 5 is a cross-sectional view of the cassette taken generally along the line V-V in FIG. 4A.
Figure 6:
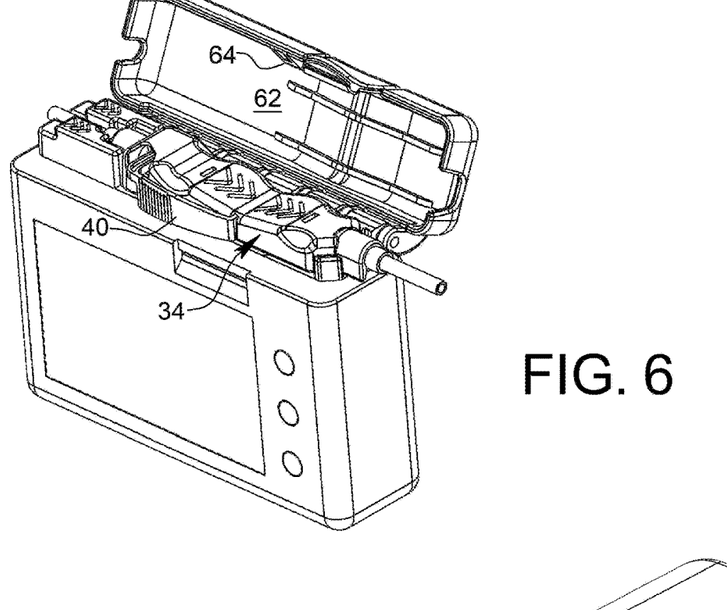
FIG. 6 is a perspective view showing the cassette loaded in the infusion pump prior to closing a door of the pump.

Cassette body 36 may include a platen surface 44 extending adjacent to at least a portion of tubing segment 32A. Platen surface 44 may or may not be flat (i.e. planar). As best seen in FIG. 5, platen surface 44 may be convex toward tubing segment 32A. For example, platen surface 44 may have a trapezoidal shape characterized by a pair of inclined end regions 44B connected by a flat central region 44A.

Deflection of pinch arm 40 between the closed position (FIGS. 3A and 3B) and the open position (FIGS. 4A and 4B) may displace movable pinch element 42 in a lateral direction relative to platen surface 44 and tubing segment 32A. With such a configuration, cassette 34 may be provided with a low profile because movement of pinch element 42 toward and away from platen surface 44 to stop and allow flow is avoided.

Cassette body may include a wall 46 having an opening 48 therethough. Pinch arm 40 may have a first portion 40A cantilevered outwardly from wall 46 to extend away from tubing segment 32A and a second portion 40B arranged to extend inwardly from a distal end of first portion 40A toward tubing segment 32A, wherein second portion 40B passes through opening 48 in wall 46. Movable pinch element 42 may be located on second portion 40B of pinch arm 40. In the embodiment shown in FIGS. 3 and 4, pinch arm 40 is deflectable away from the closed position by forcing first portion 40A of the pinch arm toward wall 46. This configuration advantageously provides an intuitive and easy structure for manually priming administration set 30 with one hand, whereby the user simply squeezes the cassette body 36 in a lateral direction to urge pinch arm 40 toward wall 46.

Movable pinch element 42 may include a movable pinch edge 42A and the fixed pinch element 38 may include a fixed pinch edge 38A, wherein the movable pinch edge and fixed pinch edge contact tubing segment 32A on opposite lateral sides of the tubing segment. The fixed pinch edge 38A and movable pinch edge 42A may be arranged to contact tubing segment 32A directly across from one another at an axial pinch location P along the tubing segment, as shown in FIG. 3B, whereby a reliable closure of tubing segment 32A is achieved when pinch arm 40 is moved to the closed position.

Cassette body 36 may include at least one grip 50 for holding tubing segment 32A adjacent to platen surface 44. For example, first and second grips 50 may be arranged near opposite ends of the platen surface 44, respectively.

Cassette body 36 may be molded or additively manufactured, for example by three-dimensional printing, as a monolithic plastic part. By way of non-limiting example, cassette body 36 may be molded from a polycarbonate or TRITAN™ brand plastic. As will be appreciated from the foregoing description, monolithic cassette body 36 includes an integrally formed free-flow protection device.

As an option, cassette 34 may further comprise a spring 52 received by cassette body 36 for providing additional spring biasing of pinch arm 40 toward the closed position when the pinch arm is deflected away from the closed position. In one embodiment, spring 52 is a leaf spring which includes a proximal end 53 and a distal end 55, and cassette body 36 includes a first slot 37 adjacent wall 46 and a second slot 39 adjacent pinch arm 40, wherein first slot 37 receives proximal end 53 of leaf spring 52 and second slot 39 receives distal end 55 of the leaf spring. According to the illustrated embodiment, second slot 39 may receive distal end 55 of leaf spring 52 with clearance between the distal end of the leaf spring and an end of the slot. First slot 37 may be proximate a cantilever location where first portion 40A of pinch arm 40 merges with wall 46.

While spring 52 is shown in one embodiment as being a leaf spring, spring 52 may be a different type of spring, for example a coil spring or a torsion spring.

Figure 7:
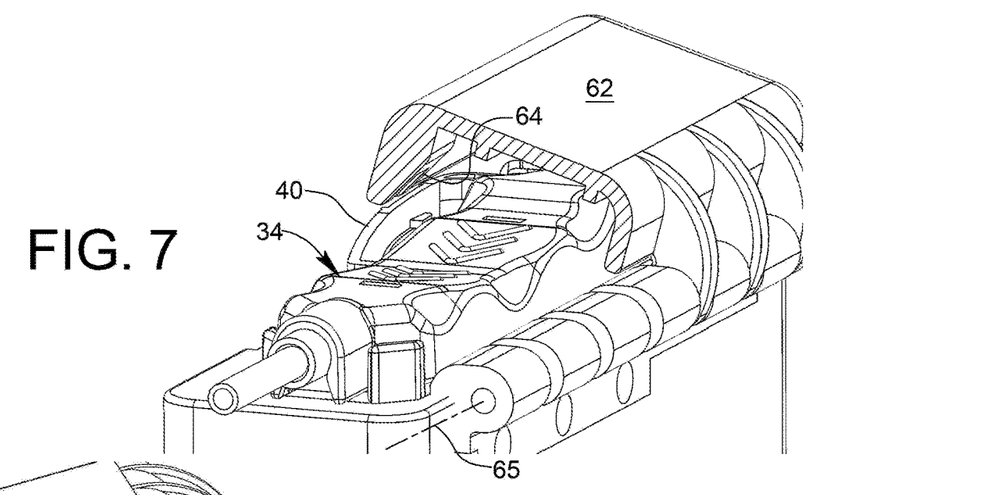
FIG. 7 is partially sectioned perspective view of the cassette and pump wherein the pump door is partially closed over the cassette.
Figure 8:
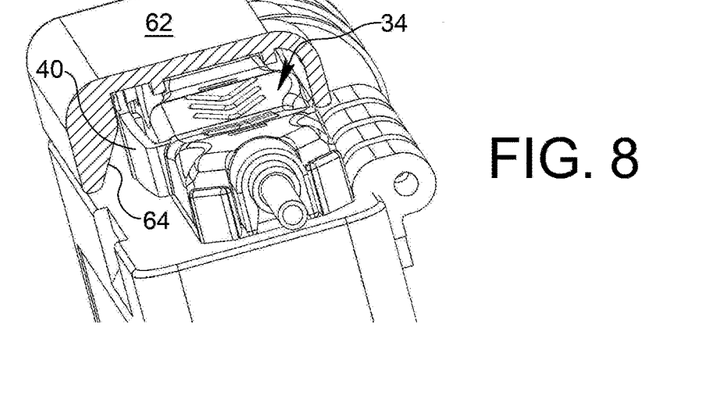
FIG. 8 is a partially sectioned perspective view of the cassette and pump wherein the pump door is fully closed over the cassette.

Loading of cassette 34 into infusion pump 10 to provide a safe fluid delivery system will now be described with reference to FIGS. 1, 7, and 8. Pump 10 may include a cassette interface 60 configured for removably receiving cassette 34, and a door 62 movable relative to cassette interface 60 between a loading position depicted in FIG. 1 and a pumping position depicted in FIG. 8. Cassette interface 60 may include a flexible, fluid-sealing membrane 61 covering pumping fingers 22 of pumping mechanism 12. To load cassette 34 in pump 10, the user places the cassette into cassette interface 60 as shown in FIG. 7 such that tubing segment 32A of cassette 34 faces membrane 61, whereby tubing segment 32A may be operatively engaged by pumping mechanism 12. As shown in FIG. 7, pinch arm 40 is in its undeflected closed position such that flow through tubing segment 32A is prevented as described above.

Door 62 may include a cam surface 64 configured to engage pinch arm 40 as door 62 is moved from the loading position to the pumping position, as indicated by the arrow in FIG. 7. Cam surface 64 may be configured such that movement of the door into the pumping position causes cam surface 64 to engage and progressively deflect pinch arm 40 inward to its open position against the natural bias of pinch arm 40 and the additional bias of optional spring 52 (if an optional spring is provided). When pump door 62 is in its pumping position as shown in FIG. 8, pinch arm 40 is held by door 62 and cam surface 64 in its open position, whereby flow through tubing segment 32A is permitted. When it is time to remove (i.e. unload) cassette 34 from pump 10, door 62 is moved from its pumping position back toward its loading position, and pinch arm 40 automatically returns under its own resiliency to its undeflected closed position. If optional spring 52 is provided, the automatic return of pinch arm 40 to its closed position is aided by spring 52. Thus, flow through tubing segment 32A is once again prevented.

In the illustrated embodiment, pump door 62 has a hinge axis 65 about which the pump door pivots between the loading position and the pumping position, and deflection of pinch arm 40 from the closed position to the open position is in a direction toward hinge axis 65. Instead of a hinged door, a sliding door may be used and configured such that sliding the door from its loading position to its pumping position will deflect pinch arm from its closed position to its open position.

While the present disclosure describes exemplary embodiments, the detailed description is not intended to limit the scope of the appended claims to the particular embodiments set forth. The claims are intended to cover such alternatives, modifications and equivalents of the described embodiments as may be included within the scope of the claims.

What is claimed is:

1. A cassette for use with a pump for delivering liquid to a patient, the cassette comprising:
   a monolithic cassette body; and
   a segment of resiliently deformable tubing mounted to the cassette body for conveying a flow of liquid;
   wherein the cassette body includes a fixed pinch element and a pinch arm having a movable pinch element;
   wherein the pinch arm has a closed position in which the movable pinch element cooperates with the fixed pinch element to deform the tubing segment to stop the flow of liquid; and
   wherein the pinch arm is resiliently deflectable away from the closed position to an open position in which the movable pinch element is positioned relative to the fixed pinch element such that the flow of liquid is permitted, wherein deflection of the pinch arm away from the closed position spring biases the pinch arm toward the closed position.

2. The cassette according to claim 1, wherein the cassette body includes a platen surface, and deflection of the pinch arm from the closed position to the open position displaces the movable pinch element in a lateral direction relative to the platen surface and the tubing segment.

3. The cassette according to claim 2, wherein the cassette body includes at least one grip for holding the tubing segment adjacent to the platen surface.

4. The cassette according to claim 3, wherein the at least one grip includes a first grip and a second grip arranged near opposite ends of the platen surface.

5. The cassette according to claim 2, wherein the platen surface is convex.

6. The cassette according to claim 5, wherein the platen surface is trapezoidal.

7. The cassette according to claim 1, wherein the cassette body includes a wall having an opening therethough, the pinch arm has a first portion cantilevered outwardly from the wall to extend away from the tubing segment and a second portion arranged to extend inwardly through the opening, and the movable pinch element is located on the second portion of the pinch arm.

8. The cassette according to claim 7, wherein the pinch arm is deflectable away from the closed position by forcing the first portion of the pinch arm toward the wall.

9. The cassette according to claim 7, further comprising a spring received by the cassette body, wherein the spring additionally spring biases the pinch arm toward the closed position when the pinch arm is deflected away from the closed position.

10. The cassette according to claim 9, wherein the spring is a leaf spring.

11. The cassette according to claim 10, wherein the leaf spring includes a proximal end and a distal end, and the cassette body includes a first slot adjacent the wall and a second slot adjacent the pinch arm, wherein the first slot receives the proximal end of the leaf spring and the second slot receives the distal end of the leaf spring.

12. The cassette according to claim 11, wherein the second slot receives the distal end of the leaf spring with clearance between the distal end of the leaf spring and an end of the second slot.

13. The cassette according to claim 11, wherein the first slot is proximate a cantilever location where the first portion of the pinch arm merges with the wall.

14. The cassette according to claim 1, wherein the fixed pinch element includes a fixed pinch edge and the movable pinch element includes a movable pinch edge, wherein the fixed pinch edge and the movable pinch edge contact the opposite sides of the tubing segment and are directly across from one another when the pinch arm is in the closed position.

15. A fluid delivery system comprising:
    a pump comprising a cassette interface and a pump door movable relative to the cassette interface between a loading position and a pumping position;
    a cassette configured for receipt by the cassette interface of the pump when the pump door is in the loading position, the cassette comprising:
        a monolithic cassette body; and
        a segment of resiliently deformable tubing mounted to the cassette body for conveying a flow of liquid;
    wherein the cassette body includes a fixed pinch element and a pinch arm having a movable pinch element;
    wherein the pinch arm has a closed position in which the movable pinch element cooperates with the fixed pinch element to deform the tubing segment to stop the flow of liquid; and
    wherein the pinch arm is resiliently deflectable away from the closed position to an open position in which the movable pinch element is positioned relative to the fixed pinch element such that the flow of liquid is permitted, wherein deflection of the pinch arm away from the closed position spring biases the pinch arm toward the closed position;
    wherein when the cassette is received by the cassette interface of the pump, movement of the pump door from the loading position to the pumping position causes the pump door to deflect the pinch arm from the closed position to the open position, and subsequent movement of the pump door from the pumping position to the loading position causes the pinch arm to automatically return from the open position to the closed position.

16. The fluid delivery system according to claim 15, wherein the pump door includes a cam surface configured to engage and progressively deflect the pinch arm as the pump door moves from the loading position to the pumping position.

17. The fluid delivery system according to claim 15, wherein the pump door has a hinge axis about which the pump door pivots between the loading position and the pumping position, and deflection of the pinch arm from the closed position to the open position is in a direction toward the hinge axis.

* * * * *